(12) United States Patent
Geier

(10) Patent No.: US 11,684,460 B2
(45) Date of Patent: *Jun. 27, 2023

(54) REFERENCE MEMBER FOR DETERMINING A POSITION OF AN IMPLANT ANALOG

(71) Applicant: Zfx GmbH, Dachau (DE)

(72) Inventor: Andreas Geier, Gargazon (IT)

(73) Assignee: ZFX GMBH, Dachau (DE)

( * ) Notice: Subject to any disclaimer, the term of this patent is extended or adjusted under 35 U.S.C. 154(b) by 1160 days.

This patent is subject to a terminal disclaimer.

(21) Appl. No.: 16/225,715

(22) Filed: Dec. 19, 2018

(65) Prior Publication Data

US 2019/0117351 A1    Apr. 25, 2019

Related U.S. Application Data

(63) Continuation of application No. 15/386,255, filed on Dec. 21, 2016, now Pat. No. 10,195,003, which is a continuation of application No. 14/062,027, filed on Oct. 24, 2013, now Pat. No. 9,554,880.

(60) Provisional application No. 61/718,462, filed on Oct. 25, 2012, provisional application No. 61/747,620, filed on Dec. 31, 2012, provisional application No. 61/800,899, filed on Mar. 15, 2013.

(51) Int. Cl.
| | | |
|---|---|---|
| *A61C 9/00* | (2006.01) | |
| *A61C 8/00* | (2006.01) | |
| *A61C 13/36* | (2006.01) | |
| *G06T 7/55* | (2017.01) | |
| *G06T 7/73* | (2017.01) | |
| *A61B 6/12* | (2006.01) | |
| *G01R 33/58* | (2006.01) | |

(52) U.S. Cl.
CPC ............. *A61C 9/0053* (2013.01); *A61B 6/12* (2013.01); *A61C 8/0001* (2013.01); *A61C 8/0093* (2013.01); *A61C 9/0046* (2013.01); *A61C 13/1016* (2013.01); *G06T 7/55* (2017.01); *G06T 7/74* (2017.01); *G01R 33/58* (2013.01)

(58) Field of Classification Search
CPC ... A61C 9/0053; A61C 9/0046; A61C 8/0001; A61C 8/0093; A61C 13/1016; A61B 6/12; G06T 7/55; G06T 7/74; G01R 33/58

See application file for complete search history.

(56) References Cited

U.S. PATENT DOCUMENTS

| | | |
|---|---|---|
| 6,225,938 B1 | 5/2001 | Hayes et al. |
| 6,558,162 B1 | 5/2003 | Porter et al. |
| 6,675,040 B1 | 1/2004 | Cosman |
| 6,790,040 B2 | 9/2004 | Amber et al. |
| 7,425,131 B2 | 9/2008 | Amber et al. |
| 7,789,664 B1 | 9/2010 | Toth |

(Continued)

OTHER PUBLICATIONS

"U.S. Appl. No. 14/062,027, Advisory Action dated Aug. 8, 2016", 3 pgs.

(Continued)

*Primary Examiner* — Nicholas D Lucchesi
(74) *Attorney, Agent, or Firm* — Sheridan Ross P.C.

(57) ABSTRACT

A reference member for determining a position of an implant analog can comprise a trapezoidal body including a first side and a substantially parallel second side. The first side can define a first dimension and the second side can define a second dimension that is greater than the first dimension.

20 Claims, 3 Drawing Sheets

(56) References Cited

U.S. PATENT DOCUMENTS

| | | |
|---|---|---|
| 7,988,449 B2 | 8/2011 | Amber et al. |
| 8,011,927 B2 | 9/2011 | Berckmans, III |
| 8,221,121 B2 | 7/2012 | Berckmans, III et al. |
| 8,353,703 B2 | 1/2013 | Amber et al. |
| 8,414,296 B2 | 4/2013 | Berckmans, III et al. |
| 8,758,015 B2 | 6/2014 | Amber et al. |
| 8,777,612 B2 | 7/2014 | Suttin et al. |
| 8,888,488 B2 | 11/2014 | Berckmans, III et al. |
| 8,926,328 B2 | 1/2015 | Suttin |
| 8,944,816 B2 | 2/2015 | Robb et al. |
| 8,944,818 B2 | 2/2015 | Robb et al. |
| 8,967,999 B2 | 3/2015 | Suttin et al. |
| 9,011,146 B2 | 4/2015 | Suttin et al. |
| 9,554,880 B2 | 1/2017 | Geier |
| 2002/0160337 A1 | 10/2002 | Klein et al. |
| 2004/0143340 A1 | 7/2004 | Tuma et al. |
| 2006/0264742 A1 | 11/2006 | Neubauer et al. |
| 2007/0092854 A1* | 4/2007 | Powell ............... A61C 13/0019 433/213 |
| 2008/0153067 A1* | 6/2008 | Berckmans ............ A61C 13/34 433/213 |
| 2008/0261168 A1* | 10/2008 | Gutman ................. A61C 11/02 433/69 |
| 2011/0183289 A1* | 7/2011 | Powell ................. A61C 9/0053 433/201.1 |
| 2012/0296613 A1* | 11/2012 | Kirchner ............. A61C 8/0083 703/1 |
| 2013/0004919 A1* | 1/2013 | Kirchner ............... G16H 20/40 433/215 |
| 2013/0189646 A1* | 7/2013 | Hochman .............. A61C 19/04 433/174 |
| 2013/0196290 A1 | 8/2013 | Herrington et al. |
| 2013/0273492 A1 | 10/2013 | Suttin et al. |
| 2014/0121500 A1 | 5/2014 | Geier |
| 2014/0229144 A1 | 8/2014 | Amber et al. |
| 2014/0302458 A1 | 10/2014 | Towse et al. |
| 2015/0037756 A1 | 2/2015 | Berckmans, III et al. |
| 2015/0104754 A1 | 4/2015 | Amber et al. |
| 2015/0104756 A1 | 4/2015 | Robb et al. |
| 2015/0111179 A1 | 4/2015 | Suttin |
| 2015/0173862 A1 | 6/2015 | Suttin et al. |
| 2015/0173870 A1 | 6/2015 | Suttin et al. |
| 2015/0190209 A1 | 7/2015 | Suttin et al. |
| 2015/0320516 A1 | 11/2015 | Suttin et al. |
| 2017/0119506 A1 | 5/2017 | Geier |
| 2019/0350684 A1* | 11/2019 | Berckmans, III .. A61C 13/0019 |
| 2020/0138518 A1* | 5/2020 | Lang ........................ A61B 5/05 |

OTHER PUBLICATIONS

"U.S. Appl. No. 14/062,027, Examiner Interview Summary dated Jul. 14, 2016", 3 pgs.

"U.S. Appl. No. 14/062,027, Final Office Action dated May 3, 2016", 8 pgs.

"U.S. Appl. No. 14/062,027, Non Final Office Action dated Oct. 28, 2015", 8 pgs.

"U.S. Appl. No. 14/062,027, Notice of Allowance dated Sep. 16, 2016", 8 pgs.

"U.S. Appl. No. 14/062,027, Response filed Jan. 18, 2016 to Non Final Office Action dated Oct. 28, 2015", 13 pgs.

"U.S. Appl. No. 14/062,027, Response filed Jul. 19, 2016 to Final Office Action dated May 3, 2016", 14 pgs.

"U.S. Appl. No. 15/386,255, Examiner Interview Summary dated Aug. 14, 2018", 3 pgs.

"U.S. Appl. No. 15/386,255, Final Office Action dated Jun. 13, 2018", 11 pgs.

"U.S. Appl. No. 15/386,255, Non Final Office Action dated Oct. 6, 2017", 10 pgs.

"U.S. Appl. No. 15/386,255, Notice of Allowance dated Sep. 27, 2018", 11 pgs.

"U.S. Appl. No. 15/386,255, Preliminary Amendment filed Jan. 23, 2017", 5 pgs.

"U.S. Appl. No. 15/386,255, Response Filed Feb. 6, 2018 to Non-Final Office Action dated Oct. 6, 2017", 9 pgs.

"U.S. Appl. No. 15/386,255, Response Filed Aug. 13, 2018 to Final Office Action dated Jun. 13, 2018", 14 pgs.

U.S. Appl. No. 14/062,027 U.S. Pat. No. 9,554,880, filed Oct. 24, 2013, Reference Member for Determining a Position of an Implant Analog.

U.S. Appl. No. 15/386,255, filed Dec. 21, 2016, Reference Member for Determining a Position of an Implant Analog.

\* cited by examiner

REFERENCE MEMBER FOR DETERMINING A POSITION OF AN IMPLANT ANALOG

CLAIM OF PRIORITY

This application is a continuation application of U.S. patent application Ser. No. 15/386,255, filed Dec. 21, 2016, which is a continuation application of U.S. patent application Ser. No. 14/062,027, filed Oct. 24, 2013, now issued as U.S. Pat. No. 9,554,880, which claims the benefit of priority under 35 U.S.C. § 119(e) of Geier, U.S. Provisional Patent Application Ser. No. 61/718,462, entitled "MATCH HOLDER AND REFERENCE BODY FOR DETERMINING A POSITION OF IMPLANTS OR ANALOGS", filed on Oct. 25, 2012, Geier, U.S. Provisional Patent Application Ser. No. 61/747,620, entitled "MATCH HOLDER AND REFERENCE BODY FOR DETERMINING A POSITION OF IMPLANTS OR ANALOGS", filed on Dec. 31, 2012, and Geier, U.S. Provisional Patent Application Ser. No. 61/800,899, entitled "REFERENCE MEMBER FOR DETERMINING A POSITION OF AN IMPLANT ANALOG", filed on Mar. 15, 2013, the contents of which are herein incorporated by reference in their entireties.

TECHNICAL FIELD

This patent document pertains generally to means for determining a position of an implant analog in three-dimensional (3-D) space.

BACKGROUND

Determining a position of an implant analog can be difficult. An implant analog body can be embedded in a working model. Currently, a reference member can be screwed to an implant analog and alignment or position of the implant analog can be determined by a plurality of scans. The reference member can be cylindrical or a conical cylinder with a flat section that can be used for orientation of the geometry of the body. The reference member can be matched to each of a number of implant analog systems. Consequently, a high degree of user skill and concentration can be required to match the reference member to each implant analog system. In order to mitigate potential for error during processing of data, the reference member alignment or position can be documented manually or taken when selecting the corresponding geometry.

Dimensions of the reference member can be constrained by adjacent teeth, such that the cylinder can be no thicker than about 5 millimeters (mm). Measurement of the reference member can be a tactile, as well as a visual, endeavor. The tactile measurement can include measuring a cover surface of the cylinder, which is defined by a circle and a plane. A center of the circle and a vector describing the position of the plane can describe a direction of the reference member. Since height of the measured cylinder can be known, the position and direction of the implant analog can be described. Visual measurement of the reference member can be scanned and software can extrude data. Also with this technique, the center of the lid surface can be obtained.

Another way to determine the position of an implant analog body can be a best fit function. In this technique, the reference member can be scanned or triangulated relative to another body.

SUMMARY

To better illustrate the reference member and related methods disclosed herein, a non-limiting list of examples is provided here:

In Example 1, a reference member for determining a position of an implant analog, comprising a trapezoidal body including a first side and a substantially parallel second side, the first side defining a first dimension and the second side defining a second dimension greater than the first dimension; an apical surface, including an apical orifice, disposed on an apical end of the trapezoidal body; and a coronal surface, including at least a first reference code and a second reference code, disposed on a coronal end of the trapezoidal body.

In Example 2, the reference member of Example 1 is optionally configured such that the apical surface and the coronal surface are integral with the trapezoidal body.

In Example 3, the reference member of any one or any combination of Examples 1-2 is optionally configured such that the apical surface and the coronal surface are formed as separate components that are coupled to the trapezoidal body.

In Example 4, the reference member of any one of or any combination of Examples 1-3 is optionally configured such that the first reference code is different than the second reference code.

In Example 5, the reference member of any one of or any combination of Examples 1-4 is optionally configured such that the first reference code is positioned between the first side and a center of the coronal surface.

In Example 6, the reference member of any one of or any combination of Examples 1-5 is optionally configured such that the second reference code is positioned between the second side and a center of the coronal surface.

In Example 7, the reference member of any one of or any combination of Examples 1-6 is optionally configured such that at least one of the first and second reference codes is one of a 12-bit code, a 32-bit code, and a 64-bit code.

In Example 8, the reference member of any one of or any combination of Examples 1-7 is optionally configured such that the first reference code and the second reference code are configured to provide an orientation of the reference member when scanned.

In Example 9, the reference member of any one of or any combination of Examples 1-8 is optionally configured such that the first and second reference codes are configured to identify a predetermined implant analog, when the reference codes are scanned.

In Example 10, the reference member of any one or any combination of Example 1-9 is optionally configured such that the first and second reference codes are configured to identify a position of a predetermined implant analog, when the reference codes are scanned.

In Example 11, the reference member of any one of or any combination of Examples 1-10 is optionally configured such that a post extending from the apical surface of the trapezoidal body, the post including a bore in communication with the apical orifice.

In Example 12, the reference member of any one or any combination of Examples 1-11 is optionally configured such that the post is configured for snap-fit or press-fit engagement with the implant analog.

In Example 13, the reference member of any one or any combination of Examples 1-12 is optionally configured such that the implant analog is accessible through a coronal orifice formed in the coronal surface of the reference member.

In Example 14, the reference member of any one or any combination of Examples 1-13 is optionally configured such that the implant analog is accessible through a coronal orifice formed in the coronal surface of the reference member.

In Example 15, a method for determining a position of an implant analog, comprising, providing or obtaining a reference member, the reference member including, a trapezoidal body including a first side and a substantially parallel second side, the first side defining a first side width and the second side defining a second side width greater than the first side width, an apical surface disposed on an apical end of the trapezoidal body, the apical surface including an apical orifice, a post extending from the apical surface of the trapezoidal body, the post including a bore in communication with the apical orifice, and a coronal surface disposed on a coronal end of the trapezoidal body, the coronal surface including at least a first reference code and a second reference code, the first and second reference codes correlated to a predetermined implant, coupling the reference member to an implant analog, including receiving the implant analog within the bore, and scanning at least the reference member with a scanner In Example 16, the method of Example 15 is optionally configured for generating a virtual geometric shape of the reference member or the predetermined implant from a plurality of scanned images.

In Example 17, the method of any one of or any combination of Examples 15 or 16 is optionally configured such that generating the virtual geometric shape includes superimposing at least a portion of the plurality of scanned images on each other.

In Example 18, the method of any one of or any combination of Examples 15-17 is optionally configured such that superimposing is based on an orientation of the first reference code and an orientation of the second reference code.

In Example 19, the method of any one of or any combination of Examples 15-18 is optionally configured such that scanning the reference member includes identifying the predetermined implant.

In Example 20, the method of any one of or any combination of Examples 15-19 is optionally configured for comparing the generated virtual geometric shape to a stored geometry of the reference member, wherein the reference member is specific to the implant analog.

In Example 21, the method of any one of or any combination of Examples 15-20 is optionally configured for positioning a virtual abutment to fit within boundaries defined by the generated virtual geometric shape.

In Example 26, a system for a determining a position of predetermined implant analog configured to be implanted in a dental cavity, and a reference member, including, a trapezoidal body including a first side and a substantially parallel second side, the first side defining a first side width and the second side defining a second side width greater than the first side width, an apical surface disposed on an apical end of the trapezoidal body, the apical surface including an apical orifice, a post extending from the apical surface of the trapezoidal body, the post including a bore in communication with the apical orifice and configured to receive the predetermined implant analog, and a coronal surface disposed on a coronal end of the trapezoidal body, the coronal surface including at least a first reference code and a second reference code, the first and second reference codes configured to provide a position of the predetermined implant analog.

In Example 27, the reference member, method, or system of any one or any combination of Examples 1-26 is optionally configured such that all elements or options recited are available to use or select from.

This Summary is intended to provide non-limiting examples of the present subject matter—it is not intended to provide an exclusive or exhaustive explanation. The Detailed Description below is included to provide further information about the present match holder, reference member, and methods.

BRIEF DESCRIPTION OF THE DRAWINGS

In the drawings, which are not necessarily drawn to scale, like numerals can be used to describe similar elements throughout the several views. The drawings illustrate generally, by way of example, but not by way of limitation, various embodiments discussed in the present document.

FIG. 2 is a cross-sectional view of the reference member, in accordance with at least one example;

DETAILED DESCRIPTION

The present disclosure describes a reference body, such as an extraoral reference body (e.g., matchholder), for determining a position of an implant analog within a mouth or cavity of a patient. The reference body described herein can be of a predetermined geometry, such that the reference body can be used with a variety of dental implant analogs. The reference body described herein can be configured to optimize the amount of space available within a working model. Further, the reference body orientation within the working model can be determined by one or more reference codes on the reference body, such that user error can be substantially mitigated. Further, the one or more reference codes can indicate or correlate to a specific style or type of implant analog. Although the following description focuses on a single tooth cavity, the described examples can also be used for multiple tooth cavities.

Figure 1A:
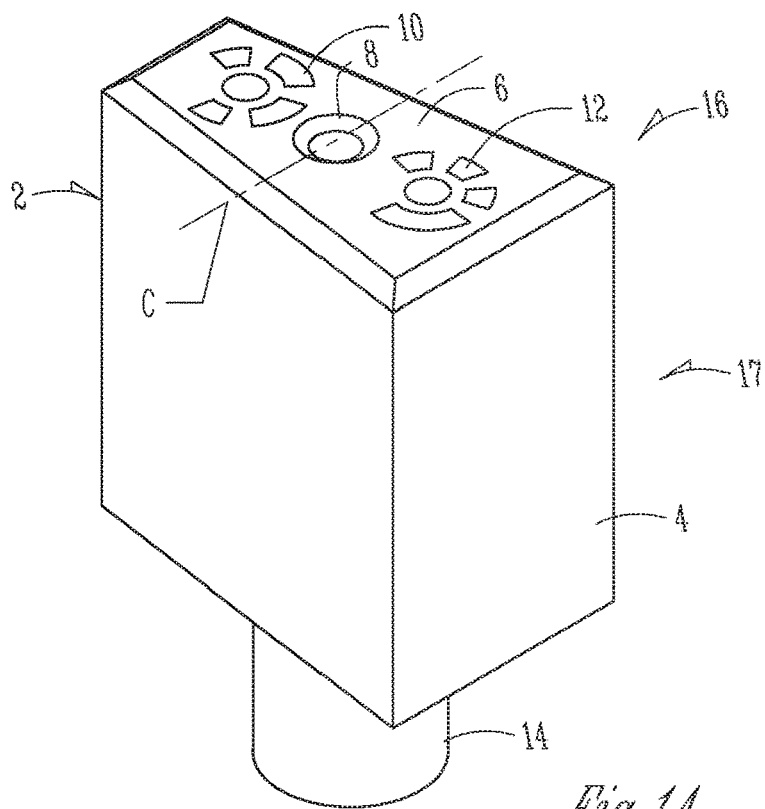
FIG. 1A is a perspective view of a reference member, in accordance with at least one example.

FIG. 1A is a perspective view of a reference member 16, in accordance with at least one example of the present disclosure. One or more of the components of the reference member 16 can be made of a biocompatible material, such as a material that does not produce a toxic, injurious, or immunological response in living tissue. Biocompatible materials can include, but are not limited to, ceramics, synthetic polymeric materials, and metallic materials such as titanium, a titanium alloy, cobalt chromium, cobalt chromium molybdenum, tantalum, or a tantalum alloy. In various examples, the reference member 16 can be reusable, such as after sterilization. In an example, the reference member 16 can be made of a polymer such as polyether ether ketone (PEEK).

As illustrated in FIG. 1A, the reference member 16 can include a trapezoidal body 17, including a first side 2, a substantially parallel second side 4, and a coronal surface 6. The trapezoidal body 17 can be configured to optimize a cavity space within the working model. The cavity space is generally constrained by the adjacent teeth and cavity shape. Typical reference members are generally cylindrical or conical cylindrical with a flat section used for orientation of the reference member. However, such cylindrical reference members are not constructed in consideration of the adjacent teeth, generally limiting a diameter of the reference body to 5 millimeters or less, such that a surface area of the flat section is less than about 19.5 mm². The trapezoidal body 17 of the reference member 16 can take into consideration the space limitation imposed by the adjacent teeth. In an example, the reference member 16, due to the trapezoidal shape, can have a surface area of the coronal surface 6 greater than about 25 mm². A larger surface area of the coronal surface 6 can allow for increased accuracy in determining a position or an orientation of the reference member 16 on the implant analog, such as providing an increased area for reference codes as described below. Further, the larger shape of the reference member 16, as compared to previous approaches, can increase accuracy of optical positioning, such as by a user, of the reference member 16 or the implant analog.

The coronal surface 6 can be integral with the trapezoidal body 17 or formed as a separate component configured to be coupled to the trapezoidal body 17. As illustrated in FIG. 1A, the coronal surface 6 can include one or more reference codes, such as a first reference code 10 and a second reference code 12. In an example, the first reference code 10 can be associated with the first side 2 of the trapezoidal body 17 and the second reference code 12 can be associated with the second side 4 of the trapezoidal body 17. The first reference code 10 can be positioned on the coronal surface 6 between a center C of the coronal surface 6 and the first side 2. The second reference code 12 can be positioned on the coronal surface 6 between the center C of the coronal surface 6 and the second side 4.

The first and second reference codes 10, 12 can be different codes, such that each reference code is uniquely identifiable optically or by a scanning device, as described herein. The first and second reference codes 10, 12 can permit a user to take an impression or a computerized visualization, such as photometrically, of an implant analog or an abutment with the use of an intraoral device that can scan the reference codes 10, 12 on the coronal surface 6 of the reference member 16. These reference codes 10, 12 can provide information to determine an orientation of the reference member 16 or the implant analog. The reference codes 10, 12 can include any type of scannable or visually discernible object or marking, such as those illustrated in FIG. 1A, including, but not limited to, bar codes or quick read codes. For instance, a reference code, such as the first and second reference codes, can include a pattern or predefined order of scannable shapes, including any geometric shape. A scannable shape can include a shape of a contrasting color or shading to the coronal surface 6, a scannable shape in at least one of infrared, ultraviolet, or visible wavelength, or any combination thereof. Further, the reference codes 10,12 can be engraved, such as by laser engraving, the coronal surface 6. The reference codes 10, 12 can include encoding such as, for example 12-bit, 32-bit, or 64-bit encoding, such that by combining the two encodings of the reference codes 10, 12, over 1900 different geometries can be described. The reference codes 10, 12 can identify, when scanned, a type or style of implant analog.

The reference member 16 can include a coronal orifice 8 extending through the coronal surface 6. The coronal orifice 8 can be configured to allow for insertion of a tool, such as a screw driver, into the trapezoidal body 17. Although the coronal orifice 8 is shown as circular, it is contemplated that orifice 8 can be any geometric shape including, but not limited to, square, rectangular, star, or the like. The coronal orifice 8 can be located anywhere on the coronal surface 6, such as in the center C.

As illustrated in FIG. 1A, the reference member 16 can include a post 14 extending from the trapezoidal body 17. As will be discussed in further detail below, the post 14 can be configured to snap fit or press fit with the implant analog.

Figure 1B:
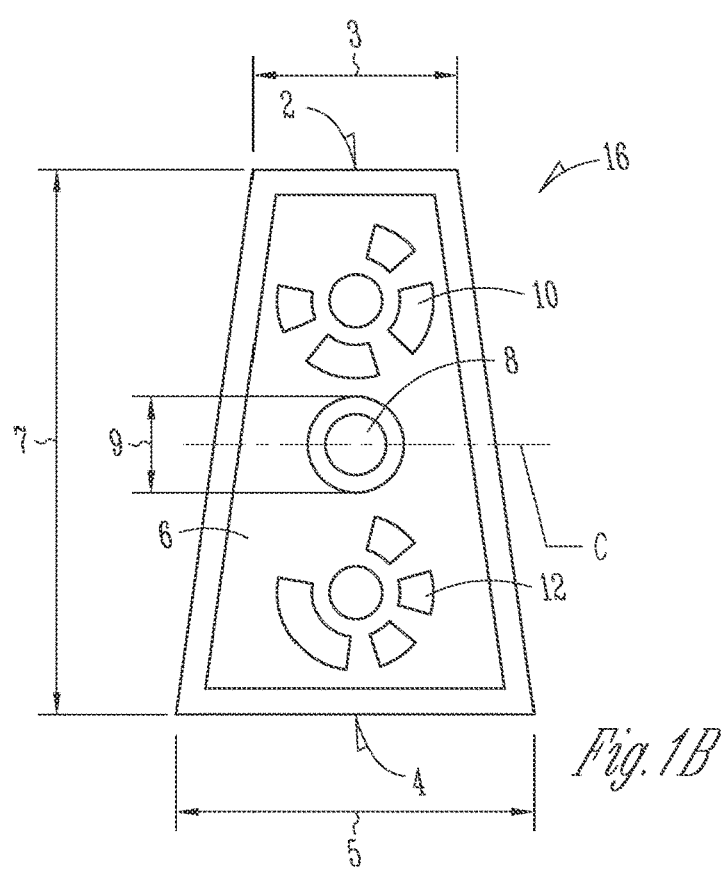
FIG. 1B is a top view of the reference member, in accordance with at least one example.

FIG. 1B is a top view of the reference member 16, in accordance with at least one example of the present disclosure. As previously discussed, the coronal surface 6 includes the first and second reference codes 10, 12 disposed toward the first side 2 and the second side 4, respectively. With reference to FIG. 1B, the first side 2 can define a first dimension 3 and the second side 4 can define a second dimension 5. The first and second dimensions 3, 5 can represent the lengths of the first and second sides 2, 4, respectively, of the reference member 16. The first dimension 3 can be less than the second dimension 5, thereby defining a portion of the trapezoidal body 17. In an example, the first dimension 3 can be less than about 5 mm, and the second dimension 5 can be less than about 7 mm. In an example, the first dimension can be about 3 mm and the second dimension can be about 5 mm. A third dimension 7, such as the length from the first side 2 to the second side 4, can be greater than one or both the first and second dimensions 3, 5. In an example, the third dimension 7 can be about 5 mm to about 10 mm. The coronal orifice 8 can define a fourth dimension 9, such as the diameter of the coronal orifice 8. In an example, the fourth dimension can be less than about 3 mm.

FIG. 2 is a cross-sectional view of the reference member 16, in accordance with at least one example of the present disclosure. As illustrated in FIG. 2, the coronal orifice 8 can be in communication with a chamber 25 of the trapezoidal body 17. A perimeter of the chamber 25 can be defined by the internal walls 23 of the trapezoidal body 17. The chamber 25 can have a trapezoidal shape that is generally similar to, but smaller than, the trapezoidal body 17. However, the internal walls 23 of the trapezoidal body 17 can be shaped and configured such that the chamber 25 defines any desired shape within the confines of the trapezoidal body 17.

At an apical end of the chamber 25 of the trapezoidal body 17, an apical surface 26 can be provided that includes an apical orifice 28. In various examples, the apical surface 26 can be integral with the trapezoidal body 17 or formed as a separate component configured to be coupled to the trapezoidal body 17. As illustrated in FIG. 2, the apical orifice 28 can be configured to retain an implant analog attachment member 24 extending through the apical orifice 28. For example, the implant analog attachment member 24 can include a head portion 27 with a diameter larger than a diameter of the apical orifice 28, such that the head portion 27 retains the implant analog attachment member 24 within the apical orifice 28. One benefit of retaining the implant analog attachment member 24 within the apical orifice 28 includes preventing the implant analog attachment member 24 from detaching or falling out of the chamber 25. The implant analog attachment member 24 can be sized and configured such that the head portion 27 can be positioned within the chamber 25, and the body portion 29 can extend through the apical orifice 28 and at least partially into a bore 22 of the post 14. In various examples, the body portion 29 of the implant analog attachment member 24 can extend beyond the post 14, or can be positioned entirely within the bore 22.

The implant analog attachment member 24 can include any fastener configured to engage the implant analog, described herein, such as a screw or bolt configured to threadably engage the implant analog. The implant analog attachment member 24 can be configured for other types of connection including, for example, a snap-fit connection or a press-fit connection. Engagement of the implant analog attachment member 24 with the implant analog can secure the reference member 16 such that no further attention, such as manual user manipulation of the reference member within the dental cavity of the working model, is required to orient the reference member 16. The implant analog attachment member 24 can be accessible through the coronal orifice 8 by a tool, such as a screwdriver.

Figure 3:
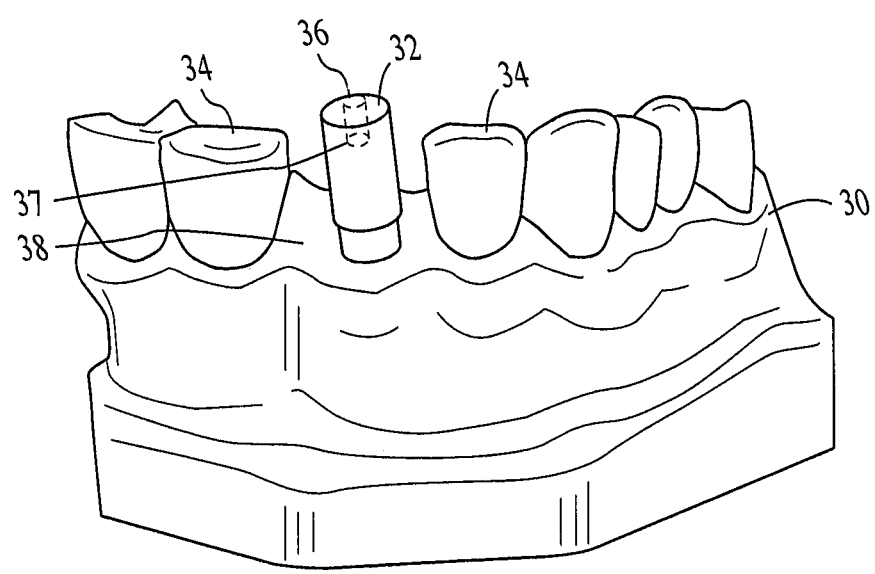
FIG. 3 is a perspective view of the implant analog engaged with a working model, in accordance with at least one example.

FIG. 3 is a perspective view of a working model 30 and implant analog 32, in accordance with at least one example of the present disclosure. The working model 30 can be a casting of a lower jaw or an upper jaw of a patient. The working model 30 can be made of a material such as a stone, polymeric, or other material. The working model can include one or more dental cavities 38, such as formed by a missing tooth. The dental cavity 38 is proximate adjacent teeth 34. The implant analog 32 can be inserted into the dental cavity 38, such as by threading or otherwise pressing the implant analog 32 into the working model 30. Further, the implant analog can include an implant analog orifice 36 disposed coronaly or in a direction away from the gum line, such that the implant analog attachment member 24 can engage the implant analog 32. The implant analog orifice 36 can include internal threading 37 configured to be threadably engaged with the implant analog engagement member 24, such that the implant analog 32 can be received within the bore 22 of the reference member 16.

Figure 4:
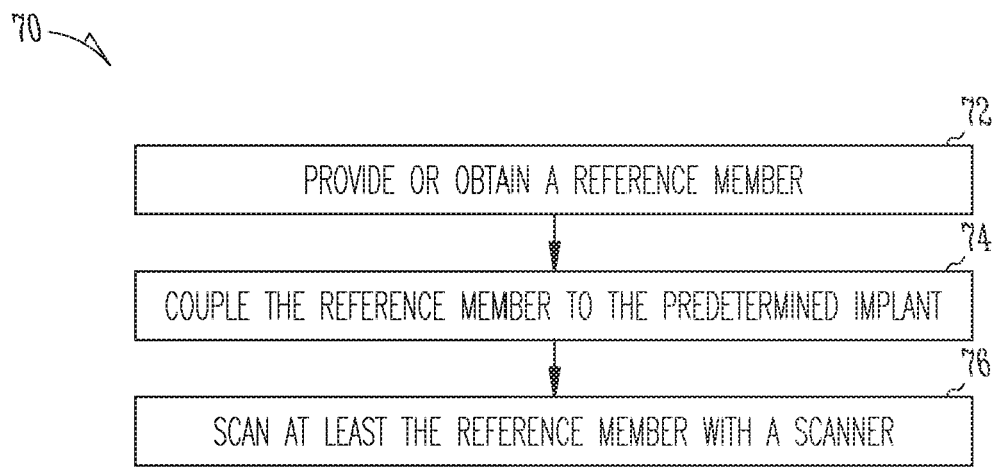
FIG. 4 is a flow diagram illustrating an example method for determining a position of an implant analog or an analog.

FIG. 4 is a flow diagram illustrating an example method 70 for determining a position of an implant analog. The method can include providing or obtaining 72 a reference member. The reference member, for example, can include a trapezoidal body including a first side and a substantially parallel second side, the first side defining a first side width and the second side defining a second side width greater than the first side width. Further, the reference member can include an apical surface disposed toward an apical end of the trapezoidal body, wherein the apical end defines an apical orifice. The reference member can include an implant analog attachment member extending through the apical orifice and a coronal surface disposed on a coronal end of the trapezoidal body, the coronal surface including one or more reference codes, such as a first reference code and a second reference code.

The method 70 can include coupling 74 the reference member to the predetermined implant, including engaging the implant analog within the bore. Engaging the implant analog can include threadably engaging an implant analog attachment member with the implant analog orifice.

The method 70 can further include scanning 76 at least the reference member with a scanner. The scanner can be a free-hand scanner that is configured to be guided by a user (e.g., not a constant, known zero, or reference point).

The method 70 can further include a number of options. For example, the method can include taking a plurality of scanned images of the reference member engaged with the implant analog. The scanned images can be partial or full images of the reference member. A virtual geometric shape of the reference member can be generated from the plurality of scanned images. Generating the virtual geometric shape can include superimposing a portion of the plurality of scanned images on one another to form a single, uniform virtual geometric shape of the reference member. Superimposing can be based on an orientation of the first reference code and an orientation of the second reference code, such that the reference codes are lined up to generate a uniform image of the reference member.

The orientation of the reference member can be described by the combination of the two reference codes and the arrangement of the reference codes on the reference member. Thus, according to the plurality of scans, the position in space of the coronal surface, the vector of the side surfaces, the orientation in space of the reference codes, or the type of geometry of the contents of the codes can be determined. Consequently, manual user input can be reduced, minimized, or unnecessary. The resulting information can be provided through a transformation matrix of the processing software, thus reducing or minimizing the error rate compared to previous approaches. The scanning of the reference member can include identifying the type or style of the implant analog, such as the reference codes an identify the implant analog.

In an example, the generated virtual geometric shape of the reference member can be compared to a stored geometry of the reference member, wherein the reference member can be specific to the implant analog. Further, the method can include positioning of a virtual abutment, such as the implant abutment in a virtual 3D environment, to fit within boundaries defined by the generated virtual geometric shape.

In view of the foregoing, the present disclosure contemplates a technique wherein the user can screw the reference member onto the implant analog, such that no further attention, such as manual manipulation of the orientation of the reference member, is necessary from the user. The reference codes on the coronal surface of the reference member can provide the position of the implant analog, such as the regardless of the orientation of the reference member. Although reference members having any suitable shape can be used, in various examples, a trapezoidal reference member can be configured to optimize the amount of space available within a dental cavity. Therefore, in an optical method, the accuracy can be improved.

The above Detailed Description includes references to the accompanying drawings, which form a part of the Detailed Description. The drawings show, by way of illustration, specific examples in which the invention can be practiced. These examples are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above Detailed Description is intended to be illustrative, and not restrictive. For example, the above-described examples (or one or more aspects thereof) may be used in combination with each other. Other examples can be used, such as by one of ordinary skill in the art upon reviewing the above Detailed Description. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

What is claimed is:

1. A device for determining a type and a position of a dental prosthesis, comprising:
    a reference member having a body having a coronal surface opposite an apical surface, a first side surface extending between the coronal surface and the apical surface, a second side surface extending between the coronal surface and the apical surface, the first side surface and the second side surface being substantially parallel and opposite each other, the coronal surface being substantially planar, and at least a first reference code and a second reference code positioned on the coronal surface, wherein the first reference code and second reference code correspond to the type and the position of the dental prosthesis; and
    a post extending from the apical surface and configured to couple the device to the dental prosthesis.

2. The device of claim 1, wherein the reference member has a coronal orifice extending through the coronal surface thereof.

3. The device of claim 2, wherein the coronal orifice is configured to allow for insertion of a tool into a cavity defined by the reference member.

4. The device of claim 1, wherein the reference member has an apical orifice extending through the apical surface thereof.

5. The device of claim 4, further comprising an attachment member comprising a fastener configured to affix the reference member to the dental prosthesis.

6. The device of claim 5, wherein the fastener extends through the apical orifice and at least partially into a bore of the post.

7. The device of claim 1, wherein the dental prosthesis comprises one of an prosthesis analog or an abutment.

8. The device of claim 1, wherein at least one of the first reference code or the second reference code are configured to provide an orientation of the reference member when scanned.

9. The device of claim 1, wherein the post is configured for snap-fit or press-fit engagement with the dental prosthesis.

10. A method for determining a type and a position of a dental prosthesis, comprising:
    providing or obtaining a reference member, the reference member having a trapezoidal body having a coronal surface opposite an apical surface, a first side surface extending between the coronal surface and the apical surface, a second side surface extending between the coronal surface and the apical surface, the first side surface and the second side surface being substantially parallel and opposite each other, the coronal surface being substantially planar and pie-shaped, the reference member including at least a first reference code and a second reference code positioned on the coronal surface, wherein the first and second reference codes correlate to the type and the position of the dental prosthesis;
    coupling the reference member to the dental prosthesis with a post extending from the apical surface of the reference member; and
    identifying the first reference code and the second reference code photometrically to determine the type and the position of the dental prosthesis.

11. The method of claim 10, further comprising generating a virtual geometric shape of the reference member or the dental prosthesis from the first reference code and the second reference code.

12. The method of claim 11, wherein generating the virtual geometric shape includes superimposing at least a portion of a plurality of scanned images on each other.

13. The method of claim 12, wherein superimposing is based on an orientation of the first reference code and an orientation of the second reference code.

14. The method of claim 11, further comprising comparing the generated virtual geometric shape to a stored geometry of the reference member, wherein the reference member is specific to the dental prosthesis.

15. The method of claim 10, wherein the reference member has a coronal orifice extending through the coronal surface thereof, and wherein the coronal orifice is configured to allow for insertion of a tool into a cavity defined by the reference member.

16. The method of claim 10, wherein the reference member has an apical orifice extending through the apical surface thereof, wherein the post includes a bore in communication with the apical orifice.

17. The method of claim 16, further comprising an attachment member comprising a fastener configured to affix the reference member to the dental prosthesis.

18. The method of claim 17, wherein the fastener extends through the apical orifice and at least partially into a bore of the post.

19. The method of claim 10, wherein the dental prosthesis comprises one of a prosthesis analog or an abutment.

20. The method of claim 10, wherein at least one of the first reference code or the second reference code are configured to provide an orientation of the reference member when scanned.

\* \* \* \* \*